(12) United States Patent
DeMeyer et al.

(10) Patent No.: US 11,626,189 B2
(45) Date of Patent: Apr. 11, 2023

(54) AGGREGATION OF COMPARTMENTALIZED CLINICAL TRIAL DATA

(71) Applicant: Clinphone Limited, Nottingham (GB)

(72) Inventors: Christopher C. DeMeyer, Lee's Summit, MO (US); Dennis M. Wijnker, Aliso Viejo, CA (US); Ron W. Dixon, Santa Ana, CA (US); Hayato Iriumi, Covington, WA (US); Dennis A. Kochanski, Costa Mesa, CA (US); Nathan Lowe, Cedar Rapids, IA (US); Solomon Shacter, Irvine, CA (US)

(73) Assignee: ClinPhone Limited, Nottingham (GB)

( * ) Notice: Subject to any disclaimer, the term of this patent is extended or adjusted under 35 U.S.C. 154(b) by 0 days.

(21) Appl. No.: 16/820,165

(22) Filed: Mar. 16, 2020

(65) Prior Publication Data

US 2020/0357088 A1 Nov. 12, 2020

Related U.S. Application Data

(63) Continuation of application No. 11/963,734, filed on Dec. 21, 2007, now Pat. No. 10,592,999.

(60) Provisional application No. 60/876,259, filed on Dec. 21, 2006.

(51) Int. Cl.
| | |
|---|---|
| G06Q 50/00 | (2012.01) |
| G16H 10/20 | (2018.01) |
| G16H 40/67 | (2018.01) |
| G06Q 50/22 | (2018.01) |

(52) U.S. Cl.
CPC .............. *G16H 10/20* (2018.01); *G06Q 50/22* (2013.01); *G16H 40/67* (2018.01)

(58) Field of Classification Search
CPC ................................. G06Q 50/00; G06F 17/60
USPC .......................................................... 705/2
See application file for complete search history.

(56) References Cited

U.S. PATENT DOCUMENTS

| | | | |
|---|---|---|---|
| 6,172,068 B1 | 1/2001 | Garvey et al. | |
| 6,173,068 B1 | 1/2001 | Prokoski | |
| 6,526,308 B1 | 2/2003 | Heikkinen | |
| 6,834,285 B1 | 12/2004 | Boris et al. | |
| 8,065,347 B1 | 11/2011 | DeMeyer et al. | |
| 10,592,999 B2 | 3/2020 | DeMeyer et al. | |
| 2001/0032060 A1 | 10/2001 | Markidan et al. | |
| 2002/0029155 A1* | 3/2002 | Hetzel | G06Q 50/24 705/2 |
| 2004/0243439 A1* | 12/2004 | Huggard | G16H 10/20 715/255 |
| 2004/0249664 A1 | 12/2004 | Broverman et al. | |
| 2005/0256745 A1 | 11/2005 | Dalton | |
| 2007/0292012 A1 | 12/2007 | Brandon et al. | |

(Continued)

OTHER PUBLICATIONS

U.S. Appl. No. 11/963,734, filed Dec. 21, 2007, DeMeyer et al.

*Primary Examiner* — Ojo O Oyebisi
(74) *Attorney, Agent, or Firm* — Wolf, Greenfield & Sacks, P.C.

(57) ABSTRACT

Embodiments of the present disclosure include a system and method of compartmentalizing some or all aspects of clinical trial data acquisition and management. Moreover, embodiments include aggregation of the compartmentalized trial data to perform business metrics, trial interaction studies, and the like.

20 Claims, 3 Drawing Sheets

(56) References Cited

U.S. PATENT DOCUMENTS

2008/0154640 A1   6/2008   DeMeyer et al.

* cited by examiner

AGGREGATION OF COMPARTMENTALIZED CLINICAL TRIAL DATA

This application is a continuation of U.S. patent application Ser. No. 11/963,734 filed on Dec. 21, 2007, entitled "Aggregation of Compartmentalized Clinical Trial Data," now U.S. Pat. No. 10,592,999, which claims the benefit of U.S. Provisional Application No. 60/876,259, filed Dec. 21, 2006, entitled "System and Method for Aggregation of Compartmentalized Clinical Trial Data." The foregoing applications are incorporated in their entirety by reference herein.

BACKGROUND

Field of the Disclosure

The present disclosure relates generally the field of data management, and specifically clinical trial data management.

Description of the Related Art

Before a new medical drug (e.g., pharmaceuticals), device (e.g., surgical instruments or implants), or procedure may be dispensed to the public, the United States Food and Drug Administration (FDA) requires that the manufacturers conduct extensive clinical trial research in order to demonstrate the clinical effectiveness, safety, and medical advantage of their products or procedures. Extensive and often complex clinical trial protocols are developed that define, for example, targeted demographics, proposed medications, patient regimens, forms for collection, types of statistically relevant data, the timing or order of events within the study, often even the layout of the reporting data, or other suitable data. These protocols are often sufficiently complex that the protocols themselves receive FDA approval or validation.

Once a protocol is developed and approved, companies design electronic data capture and data management solutions to manage the ever burgeoning amount of data gathered. In general, such data capture and data management solutions capture data from geographically disparate clinicians or study participants defining many points of data entry, potentially across many software and hardware platforms.

As one may suppose, manufacturers invest millions of dollars conducting the foregoing clinical trials before they receive any revenue from a sale of their products. For example, a rough estimate may be as long as 12 to 15 years to bring a drug to market at a cost of over $800 million. Accordingly, sponsors are eager to lower the cost and complexity associated with clinical trials, and sponsors are almost fanatical in their desire to avoid corruption of acquired clinical trial data. An entire industry of companies, called Contract Research Organizations (CROs), has developed that specialize in the execution of clinical trials and in the capture and management of clinical trial data on behalf of the manufacturers.

Whether performed by a CRO or by manufacturers themselves, the systems that acquire and manage clinical trial data often are also approved or validated by FDA. Such validation ensures that acquired clinical trial data is protected from fraud, corruption, software upgrade errors, and commingling. However, drawbacks occur when a system upgrade is desired even though one or more clinical trials may be years into execution within the system. For example, when something fails during an upgrade, or when an upgraded system fails to pass the FDA validation, the data for the already executing trials may be deemed corrupted. Clearly, such a finding of corruption can result in losses of millions of dollars in retesting, recollecting data, and perhaps most significant, can result in a significant loss of time. Moreover, even if the upgrade is successful, translation from an old system to the new upgraded system may include significant brute force computing to organize often vast amounts of collected data. Based simply on the possibility of harm to the existing data, manufacturers and CROs are often unwilling to upgrade systems where trials are in progress. Also, because trials can start at any time and have wildly varying durations, finding a time for upgrades may be impractical.

Based on the foregoing, manufacturers and CROs have begun to compartmentalize backend databases, Compartmentalization segments the various trials' data and each database can be upgraded individually. However, such systems are still exposed to corruption issues from, for example, code validations. Moreover, such a system increases complexity by allowing for code bases and database to be different upgrades or version for the same study.

SUMMARY

The present disclosure includes embodiments of systems for acquiring and managing clinical trial data where a code base and a database is compartmentalized to one or more clinical studies. Compartmentalization of the code base advantageously provides separation for acquisition and management of clinical trial data for each or a number of related clinical trials. Such compartmentalization advantageously segregates system upgrades and the like from potentially corrupting data across clinical trials. Moreover, segregation allows new trials to begin with the newest code base available, while still allowing older clinical trials, which are already operating effectively, to continue with an older code base.

In an embodiment of the disclosure, a system compartmentalizes code bases and databases associated with each or a small group of studies, and also includes an aggregation application provides visibility of data across a selected group or many clinical trials, Providing aggregation advantageously provides CROs and other users the ability to gather and monitor valuable information, such as business metrics indicative of efficiencies in running trials. In an embodiment, the aggregation application is also FDA validated, thereby advantageously ensuring interactions with clinical trial databases do not risk corrupting previously acquired clinical trial data. Thus, in an embodiment, CROs and other users enjoy premium functionality and efficiency monitoring, along with the current upgrades for new studies, all without lessening the advantages of the compartmentalized clinical trial code and database solution.

In an embodiment, a system for aggregating segregated data in a clinical trial setting reduces the possibilities of data corruption. The system includes multiple trial data stores that store clinical data from a single clinical trial or set of related clinical trials. A server system runs a code base specific to each trial or set of related trials, which accepts clinical trial data from doctors and hospitals and updates the appropriate trial data store. Embodiments of the system advantageously include an aggregation module. In an embodiment, the aggregation module is capable of retrieving copies of clinical data from one or more trial data stores for business metrics, trial interaction studies, and the like.

For purposes of summarizing the disclosure, certain aspects, advantages and novel features of the disclosure have been described herein. Of course, it is to be understood that not necessarily all such aspects, advantages or features will be embodiment in any particular embodiment.

BRIEF DESCRIPTION OF THE DRAWINGS

A general architecture that implements the various features of the present disclosure will now be described with reference to the drawings. The drawings and the associated descriptions are provided to illustrate embodiments of the disclosure and not to limit its scope. Throughout the drawings, reference numbers are re-used to indicate correspondence between referenced elements.

DETAILED DESCRIPTION

Figure 1:
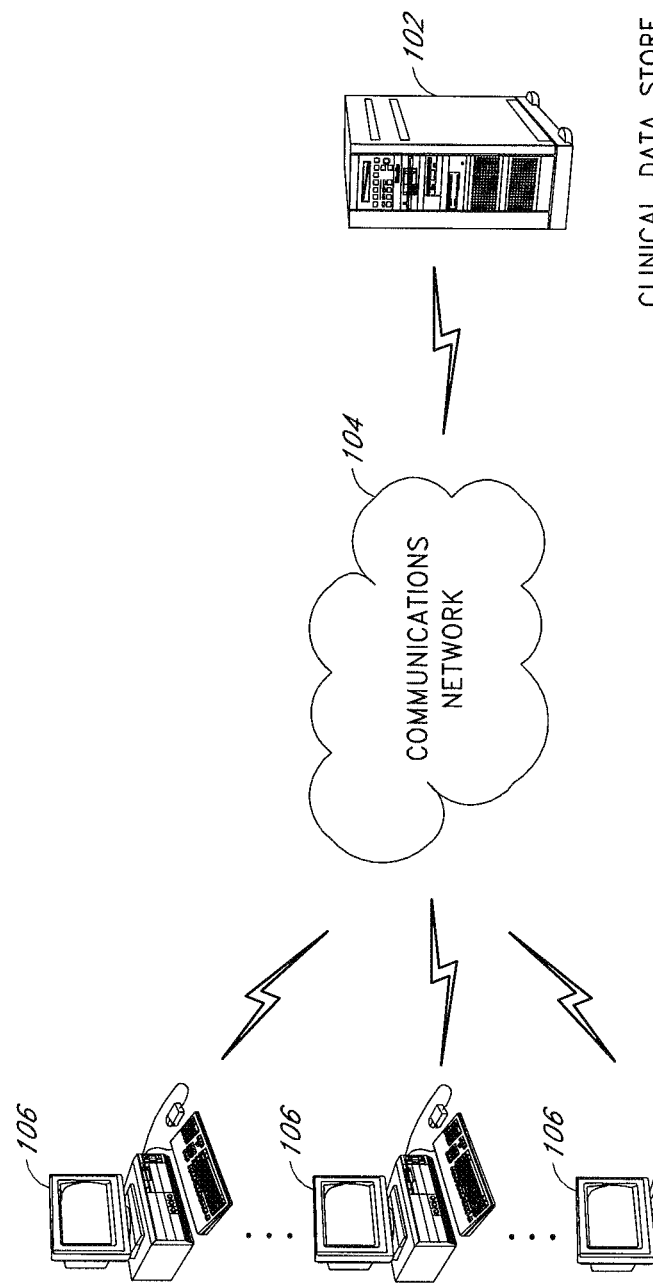
FIG. 1 illustrates an embodiment of a high-level diagram of a clinical trial data management system.

A clinical trial data management system, under an embodiment of the present disclosure, comprises a clinical data store that is capable of accepting and managing the clinical data from numerous disparate clinical trials. In an embodiment, this clinical data store connects with distributed remote data entry systems through a network, such as the Internet, and the remote data entry systems are personal computers, workstations, or web-enabled personal digital assistants (PDAs) at hospitals, clinics, or doctor's offices participating in a clinical trial. In an embodiment, this data store includes a web server running a program capable of serving dynamic web pages to the remote data entry systems that access the program via a web browser. In this way the clinical data store and remote data entry systems interact to accomplish tasks, such as, for example, patient sign-up, accepting or rejecting patients as study participants, receiving participant data, and providing drug type, dosage, or other instructions for the doctor and participant.

In an embodiment, a clinical data store comprises a server system that executes code bases to manage one or a number of discrete trials, which store data in one or a number of discrete physical databases. Regardless of the number of physical databases, the clinical data store provides disparate virtual databases for each clinical trial being managed. In an embodiment, each clinical trial also includes its own management code base used in accessing and updating that clinical trial's data. This segmented code allows newer trials to run newer code versions without risking corruption of other trials and can allow individual trials to be upgraded on a trial-by-trial basis. The overall separation helps ensure the integrity and security of the clinical data that is reported. The clinical data store also comprises an aggregation module to allow the manager of the clinical data store to perform business metrics on the system or otherwise analyze system-wide data while reducing any risk of the corruption of the data by maintaining the segmented clinical trials. In an embodiment, the aggregation module preferably operates as an object request broker or a middle tier web broker. Upon request, the aggregation module pulls the requisite data from each clinical trial database and processes the requested query.

Systems and methods representing various embodiments and example applications of the present disclosure will now be described with reference to the drawings. Corresponding numbering indicates corresponding parts, and often the leading digit indicates the figure in which an element first appears.

For purposes of illustration, some embodiments will be described in the context of clinical trial studies conducted by CROs. The present disclosure, however, is not limited by the type of environment in which the systems and methods are used, and the systems and methods may be used in other environments, such as, for example, medical studies run by manufacturers themselves, foreign medical studies, non-medical research studies, or other suitable environments. It is also recognized that in other embodiments, the systems and methods may be implemented as a single module and/or implemented in conjunction with a variety of other modules and the like. Moreover, the specific implementations described herein are set forth in order to illustrate, and not to limit, the disclosure.

Overview

As shown in FIG. 1, in an embodiment, the system according to the disclosure comprises a clinical data store 102 capable of connecting, through a communications network 104 such as the Internet, with any of a number of various remote data entry systems 106. Clinical trials are conducted by various doctors, hospitals, clinics, and the like. Ideally each such location would include at least one remote data entry system 106 connected to the Internet 104 and executing a web browser such as, for example, Internet Explorer, Netscape Navigator, or FireFox. A doctor, staff, or technician utilizes the remote data entry system 106 to enter information about patient procedures, or other data desired to be collected during the clinical trial.

Sample Operation

In an example clinical trial, Pharmaceutical Company has developed a new drug that it believes reduces the likelihood of a recurrence of skin cancer in patients that have contracted it previously. In order for the Company to be able to market this new drug, Topical Compound, the company sponsors one or more clinical trials to obtain FDA approval of the Topical Compound. The trial includes a number of hospitals and clinics throughout the country thereby involving a large, diverse population sample. The data is preferably electronically collected in a central location or eventually aggregated to provide the complete results of the study. FDA regulations provide that this collected electronic clinical trial data be stored and managed according to strict guidelines to ensure accuracy and integrity. The Pharmaceutical Company may advantageously use one or more CROs to manage these clinical trials.

In this example, the Company contacts CRO, which may utilize the presently disclosed system in managing its clinical trials. The CRO configures systems and software for its clinical data store as a web server, accessible through Internet-connected computing devices to the doctors, clinics, hospitals, and the like participating in the study. Patient, who has had melanomas removed before, goes to his doctor, who is involved with CRO in the study for the Topical Compound. The Patient's doctor recommends participation in the Topical Compound trial. The doctor logs on to CRO's Topical Compound web site, and enters the Patient's information, including, for example identification, health history, and other relevant data. Based on the information gathered from the Patient the doctor determines whether the patient is a possible candidate for the study. As an alternative, in an embodiment, the information gathered may be entered into the system and uploaded to the clinical data store where the information is checked against qualifying parameters to determine if the Patient is eligible to be a study participant. If the Patient is enrolled in the study, each time the Patient returns, the doctor again logs onto CRO's Topical Compound website and enters additional information about the Patient, such as heart rate, blood pressure, skin appearance, complaints, observations, potential side effects, or other information designated by the study. This data is stored in a study specific database for later compilation and submission to the FDA.

Each CRO may be involved in any number of related or non-related clinical trials simultaneously, each of which may be at a different stage or timeframe. The clinical data store manages each individual trial. Moreover, the system may compartmentalize some or all of the trials from one another through storage on physically disparate databases, through the creation of multiple virtual databases, or the like. Because trials start at different times and last for different durations, there are generally few, if any, good times to upgrade some or all of the system. Thus, in an embodiment, a system compartmentalizes databases and code bases for each compartmentalized trial. In an embodiment, compartmentalization employs a Microsoft's .NET architecture, although an artisan will recognize other solutions for compartmentalization. This compartmentalization is advantageous to reduce a possibility of data loss, corruption, or the like.

CROs and others often closely monitor business and other metrics across many trials to increase efficiencies in managing clinical trials. In an embodiment, the data store also includes an aggregation module or application. The aggregation module maintains the compartmentalization of the clinical trials but can access data across compartmentalized trials and generate any desired metrics.

Clinical Data Management System

The clinical data management system of the present disclosure includes an aggregation module associated with the clinical data store 102 that allows CROs to access data from the disparate databases in order to generate business metrics or other tests on the data while maintaining a reduced risk of corruption. In an embodiment, the aggregation module employs "read" access to the clinical trial databases to further reduce the likelihood of data contamination.

As stated, an embodiment of the clinical data management system is a distributed computer system comprising a central clinical data store 102 and at least one remote data entry system 106 connected by a communications network 104.

Clinical Data Store 102

Figure 2:
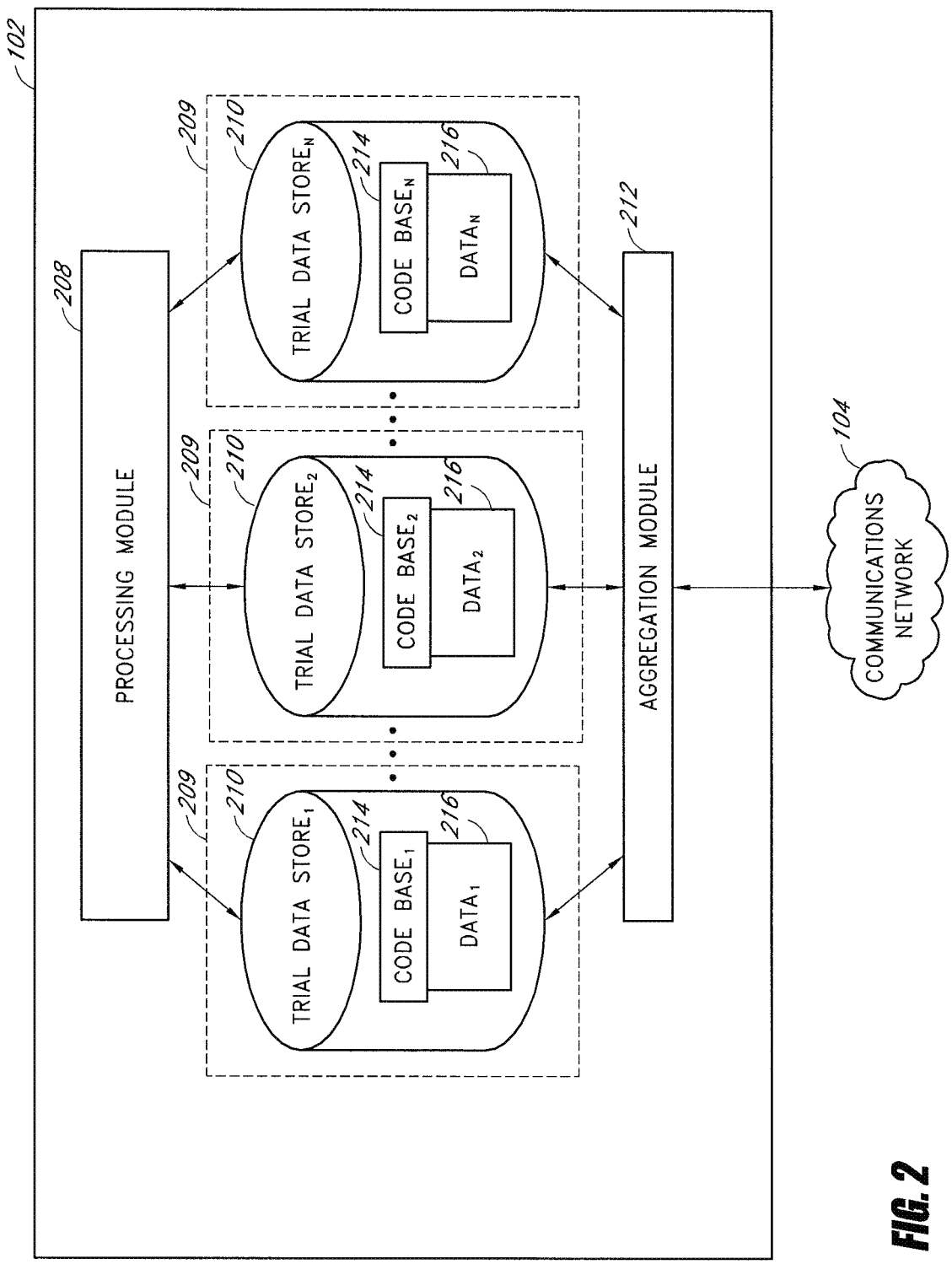
FIG. 2 illustrates an embodiment of a high level block diagram of a clinical data store server according to the present disclosure.

Turning to FIG. 2, clinical data store 102 comprises a server system 208 managing data associated with at least one clinical trial 209, and an aggregation module 212. Clinical Trial 209 comprises a trial data store 210, clinical trial data 216, and a code base 214. In an embodiment, the store 102 comprises a plurality of clinical trials 209. In an embodiment, the clinical data store 102 comprises a secure web server allowing, for example, the remote data entry systems 106, to interact with the clinical trial data 216 as part of web pages after gaining access through a login and password. The clinical data store 102 also provides web forms for the entry of clinical trial data, the remote data entry systems 106 submit the completed forms, and clinical data store 102 stores the data in the appropriate clinical trial 209's trial data store 210. In other embodiments, the clinical data store 102 and remote data entry systems 106 may act as server and clients, respectively, such as with a Java, JavaScript, Jscript or other programming language-based applet or stand alone application. In an embodiment, data entry occurs at the clinical data store 102 itself, thereby alleviating the need for a server-client relationship. In an embodiment, some or all of the foregoing functions may be controlled by individual clinical trial code bases 214 executing on the server system 208.

Server System 208

Server System 208 may be viewed as the nerve center of the present system. In an embodiment, the server system 208 executes various code bases 214 that control the entry and management of data received from remote data entry systems 106 and stored in associated trial data stores 210, As stated, the server system 208 can serve or accept HTTP or similar requests from remote data entry systems 106 and respond with appropriate html, active server pages, Java, J-script, similar applets, or other suitable data. In an embodiment, the server system 208 has separate home or entry pages for each of the clinical trials 209 being managed, and thus a user's initial web page request (or the requested URI) can be uniquely associated with a particular clinical trial 209's code base 214. In an embodiment, a single login screen is utilized for all trials and the entered login and/or password are reviewed by the server system 208, which then determines the appropriate clinical trial or trials to which that user may have access.

In an embodiment, server system 208 is capable of running various code bases 214 to access, read, and write to associated trial data stores 210. As noted, Microsoft's .NET platform is one platform well-suited to such tasks. However, one of skill in the art will recognize from the disclosure herein that other platforms, programs, modules, and the like may also be utilized to accomplish similar functions. In an embodiment, appropriate code base $214_N$ executes on server system 208 to manage and control access to the trial data stores $210_N$. In an embodiment, code base $214_N$ processes a login and password from any remote data entry system 106 attempting to gain access to clinical trial $209_N$ to help reduce unauthorized accessing and/or updating of clinical data. In an embodiment, a password and login to server system 208 controls which clinical trial $209_N$'s data can be viewed and/or edited. The code base $214_N$ can advantageously accept input data from the remote data entry systems 106 and store data in the appropriate trial data store $210_N$.

In an embodiment, execution of the code base 214 includes tasks such as serving web pages, accepting data from and providing data to remote data entry systems 106, and communicating with the associated trial data store(s) 210. In an embodiment, each code base $214_N$ is constrained to its own components. Those components may include an instruction set, object model, memory cache, code services, or the like. The constraint may be accomplished with or without server virtualization. Example virtualization solutions can be obtained from VMware (Server, Infrastructure 3) and Microsoft (Virtual Server 2005), although an artisan will recognize from the disclosure herein any of a number of publicly available or proprietary solutions that may provide virtualization.

In an embodiment, any code base $214_N$ may be altered, added, and/or deleted from server system 208 without affecting the other code bases 214. Alterations can include upgrades, patches, bug fixes, reversions, and the like. In such an environment, alterations of one code base does not cause the other code bases to need revalidation. Validations of code bases are often used to consider clinical trial data valid, but as discussed herein, revalidation of the code base can be costly and/or time-consuming, particularly so if a validation fails, thereby rendering any associated clinical trial data invalid.

Server system 208 may be comprised of a single processor or multiple processors working in conjunction, running suitable software capable of performing the required operations. Alternatively, server system 208 may be a circuit board with hard-coded instructions. The server system 208 may also be discerned by one of ordinary skill in the art from the description herein. The ability for server system 208 to run multiple code bases 214 is advantageous, because it is typically a more cost- and resource-efficient solution than setting up individual servers for each clinical trial.

Trial Data Stores 210

The trial data stores 210 may include a series of physically disparate databases—such as a networked group of server databases, or databases housed on individual hard drives—or virtual databases, segmented on the same hard drive(s). In an embodiment, each trial data store 210 comprises a database including the data 216 of a plurality of clinical trials. An artisan will understand from the disclosure herein that each trial data store 210 can include different data 216 based on the study with which it is associated. Generally, however, data 216 can include a plurality of patient or clinical trial subject entries. Each entry can include information such as, for example, patient initials, a patient identification number, patient history, drug or treatment dosage information, vitals, observations, side effects, physician notes, or other suitable information. In an embodiment, data 216 is encrypted to help protect the integrity of the information and lessen unauthorized tampering with it.

Aggregation Module 212

With the various clinical trials segmented as the system provides, it may be desirable to access data from two or more of the trials to, for example, perform global business metrics, improve trial management, assess clinical trial interactions, and other suitable tasks. In an embodiment, aggregation module 212 advantageously creates a copy of trial data. Each time an update is received through server system 208 for any of the clinical trials, it would also send the same update to the aggregation module. In an embodiment, the aggregation module has its own version of the data to manipulate without needing to access a trial data store. While copying ensures integrity of the trial data, it may use twice the amount of storage and significant processing time for relatively little use.

In an embodiment, the aggregation module 212 retrieves information from the trial data stores 210 on a limited basis and, more preferably, only retrieves information from trial data stores 210 when called to perform specific tasks. The aggregation module 212 can perform read only access to the trial data stores. Without an ability to write over data, the aggregation module 212's impact on the trial data stores 210 is diminished. The aggregation module 212 itself can be tested and validated assuring that the aggregation module's interactions with the rest of the clinical data store 102 will not cause data corruption, in addition, in an embodiment, the aggregation module 212 may use pointers, metadata, indexes, information about data, or other replication or data manipulation tools known to an artisan from the present disclosure to perform queries on aggregated data without actually copying or moving data from their segregated and protected data stores 210. Various combinations of the foregoing embodiments may also be apparent to those of ordinary skill from the present disclosure.

The aggregation module 212 may comprise one or more software applications residing on a computer readable medium, the instructions of which allow a computer to perform the various tasks discussed herein. The aggregation module 212 may comprise an integrated component of the clinical data management system or it may be created as a stand-alone application, process or the like. The module 212 may be implemented on the same or similar hardware as the clinical data store 102; any hardware specific to either the server system 208 or the trial data stores 210; on its own distinct hardware; combinations of the same or the like. An artisan will understand from the disclosure herein that some or all of these variations may be found in different embodiments.

Network Interface Module

The clinical data store 102 may also include a network interface module (not shown) that communicates with the clinical data store 102 to facilitate communication between the clinical data store 102 and the remote data entry systems 106 via the communications network(s) 104.

The network interface module may utilize a variety of network protocols. In an embodiment, the network interface module includes the Hypertext Transfer Protocol (HTTP). Other types of network communication protocols can be used, such as, for example, HTTPS, FTP, SMTP, TCP/IP, or other suitable protocols.

Input and Output Devices

The clinical data store 102 can communicate with a set of input and output devices, Input device(s) may include, for example, a keyboard, roller ball, pen and stylus, mouse, trackball, voice recognition system, pre-designated switches or buttons, or other suitable devices. The input device(s) may also include a touch screen associated with an output device. Textual or graphic information can be entered by the user through the input device. The output device(s) may include, for example, a speaker, a display screen, a printer, a voice synthesizer, or other suitable devices.

Clinical Data Store 102 System Information

The clinical data store 102 can include a conventional general purpose single-chip or multi-chip microprocessor such as, for example, a Pentium® processor, a Pentium® II processor, Pentium® III processor, Pentium® IV processor, a Pentium® Pro processor, an Intel Core Duo, an Intel Core 2 Duo, an xx86 processor, an 8051 processor, a MIPS® processor, a Power PC® processor, an ALPHA® processor, or other suitable personal computer or general purpose microprocessor. In addition, the microprocessor can be any special purpose microprocessor such as, for example, a digital signal processor, FPGA, ASIC, or other suitable special purpose microprocessor. Furthermore, the clinical data store 102 can be used in connection with various operating systems such as: Microsoft® Windows® 3.X, Microsoft® Windows 95, Microsoft® Windows 98, Microsoft® Windows® NT, Microsoft® XP, Microsoft® Windows® CE, Palm Pilot OS, OS/2, Apple® MacOS®, Apple® OS X™, Disk Operating System (DOS), UNIX, Linux®, VxWorks, or IBM® OS/2®, Sun OS, Solaris OS, IRIX OS operating systems, or other operating systems.

In an embodiment, the clinical data store 102 is a server, personal computer, a laptop computer, a portable computing device, a computer workstation, a local area network of individual computers, an interactive kiosk, a personal digital assistant, an interactive wireless communications device, a handheld computer, an embedded computing device, or other suitable computing device.

As can be appreciated by one of ordinary skill in the art from the present disclosure, the clinical data store 102 can include various sub-routines, procedures, definitional statements, and macros. The foregoing modules may be separately compiled and linked into a single executable program. However, it is to be appreciated by one of ordinary skill in the art from the present disclosure that the processes performed by the modules can be redistributed to other modules, combined together in a single module, made available in a shareable dynamic link library, or partitioned in any other logical way. For example, in an embodiment, the server system 208 and the network interface module are integrated into a single executable module. Furthermore, for example, in an embodiment, the server system 208 is maintained in a dynamic link library that is separate from the network interface module. In addition, the server system 208, the network interface module, the aggregation module 212, and/or the trial data stores 210 can be an "application program," can reside as part of the operating system for the device, or can reside partly as both.

As used herein, the word module refers to logic embodied in hardware or firmware, or to a collection of software instructions, possibly having entry and exit points. Furthermore, the modules can be written in any programming language such as, for example, VB.NET, C, C++, C#, BASIC, Pascal, Java, FORTRAN, or other suitable language. The modules can be compiled and linked into an executable program, installed in a dynamic link library, or can be written in an interpreted programming language such as BASIC, Perl, or Python. It will be appreciated from the disclosure herein that software modules can be callable from other modules or from themselves, and/or can be invoked in response to detected events or interrupts. Software instructions may be embedded in firmware and stored in a device, such as, for example, an EPROM, flash, or other suitable device. Hardware modules can be comprised of connected logic units, such as gates and flip-flops, and/or can be comprised of programmable units, such as programmable gate arrays or processors. The modules described herein are preferably implemented as software modules, but can be implemented in hardware or firmware.

Remote Data Entry Systems 106

In an embodiment, the remote data entry systems 106 provide remote access to information stored in the clinical data store 102. In an embodiment, a remote data entry system 106 is a PC comprising at least one each of input and output devices as well as a network interface module for communications with the clinical data store 102. In an embodiment, the remote data entry systems 106 and management server 102 reside on the same physical machine, such as a PC. In such a case a network interface module may not be required; a single processor may perform the actions of both the remote data entry systems 106 and the clinical data store 102 and/or internal communications may be sufficient in such an embodiment. Additionally, a remote data entry system 106 need not be a PC but can be any of a variety of devices, as discussed below.

In an embodiment, a user may utilize a remote data entry system 106 to electronically send and receive data from the management server 102, via a browser module (not pictured). The remote data entry systems 106 can send and receive data using one of any number of network protocols. In an embodiment, the request comprises a Hypertext Transfer Protocol (HTTP) request. However, other types of network communication protocols can be used. In an embodiment, the remote data entry systems 106 include some or all of the programs and/or data stored on the management server 102.

Browser Module

In an embodiment, remote data entry systems 106 include a browser module (not shown). The browser module can present information to the user such as, for example, clinical trial data, patient information and registration forms, data submission forms, or other suitable information. The browser module and/or a web page accessible via the browser module can allow the user to request additional data, add data, delete data, and/or modify data for the clinical trial.

The browser module can be implemented as a module that uses text, graphics, audio, video, and other media to present data and to allow interaction with the data via the communications network. The browser module can be implemented as a combination of an all points addressable display such as a cathode-ray tube (CRT), a liquid crystal display (LCD), a plasma display, or other types and/or combinations of displays. In addition, the browser module can communicate with input devices and can also include software with appropriate interfaces which allow a user to access data through the use of stylized screen elements such as, for example, menus, windows, dialog boxes, toolbars, controls radio buttons, check boxes, sliding scales, or other suitable elements. Furthermore, the browser module communicates with a set of input and output devices to receive signals from the user. It is recognized that in other embodiments, the browser module may be implemented as a general interface that does not include access to the communications network.

Network Interface Module

The remote data entry systems 106 can also include network interface modules (not shown) to facilitate communication with the clinical data store 102 via the communications network.

The network interface module can utilize a variety of network protocols. In an embodiment, the network interface module includes the Hypertext Transfer Protocol (HTTP). Other protocols can be used, such as, for example, TCP/IP, FTP, HTTP, HTTPS, or other suitable protocols. The network interface module can include a modem, Ethernet (NIC) card, wireless modem, cable modem, or other suitable network interfaces.

Input and Output Devices

In an embodiment, the remote data entry system 106 communicates with a set of input and output devices. For example, the input device(s) can include, for example, a keyboard, roller ball, pen and stylus, mouse, trackball, voice recognition system, pre-designated switches or buttons, or other suitable devices. The input device(s) can also include a touch screen associated with an output device. Textual or graphic information can be entered by the user through the input device. The output device(s) can include, for example, a speaker, a display screen, a printer, a voice synthesizer, or other suitable device.

Remote Data Entry System 106 Information

The remote data entry system 106 can include a conventional general purpose single-chip or multi-chip microprocessor such as, for example, a Pentium® processor, a Pentium® II processor, Pentium® III processor, Pentium® IV processor, a Pentium® Pro processor, an Intel Core Duo, an Intel Core 2 Duo, an xx86 processor, an 8051 processor, a MIPS® processor, a Power PC® processor, an ALPHA® processor, or other suitable personal computer or general purpose microprocessor. In addition, the microprocessor can be any special purpose microprocessor such as, for example, a digital signal processor, FPGA, ASIC, or other suitable special purpose microprocessor. Furthermore, the remote data entry systems 106 can each be used in connection with various operating systems such as: Microsoft® Windows® 3.X, Microsoft® Windows 95, Microsoft® Windows 98, Microsoft® Windows® NT, Microsoft® XP, Microsoft® Windows® CE, Palm Pilot OS, OS/2, Apple® MacOS®, Apple® OS X™, Disk Operating System (DOS), UNIX, Linux®, VxWorks, or IBM® OS/2®, Sun OS, Solaris OS, IRIX OS operating systems, or other operating systems.

In an embodiment, the remote data entry systems 106 is a personal computer, a laptop computer, a Blackberry® device, a portable computing device, a server, a computer workstation, a local area network of individual computers, an interactive kiosk, a personal digital assistant, an interactive wireless communications device, a handheld computer, an embedded computing device, or other suitable computing device.

The system can include various sub-routines, procedures, definitional statements, and macros. The foregoing modules can be separately compiled and linked into a single executable program. However, it is to be appreciated by one of ordinary skill in the art from the present disclosure that the processes performed by the modules can be redistributed to other modules, combined together in a single module, made available in a shareable dynamic link library, or partitioned in any other logical way. For example, in an embodiment, the browser module and the network interface module are integrated into a single executable module. Furthermore, for example, in an embodiment, the browser module is maintained in a dynamic link library that is separate from the network interface module. In addition, browser module, and/or the network interface module can be an "application program," can reside as part of the operating system for the device, or can reside partly as both.

Methods of Managing Clinical Trial Data

Figure 3A:
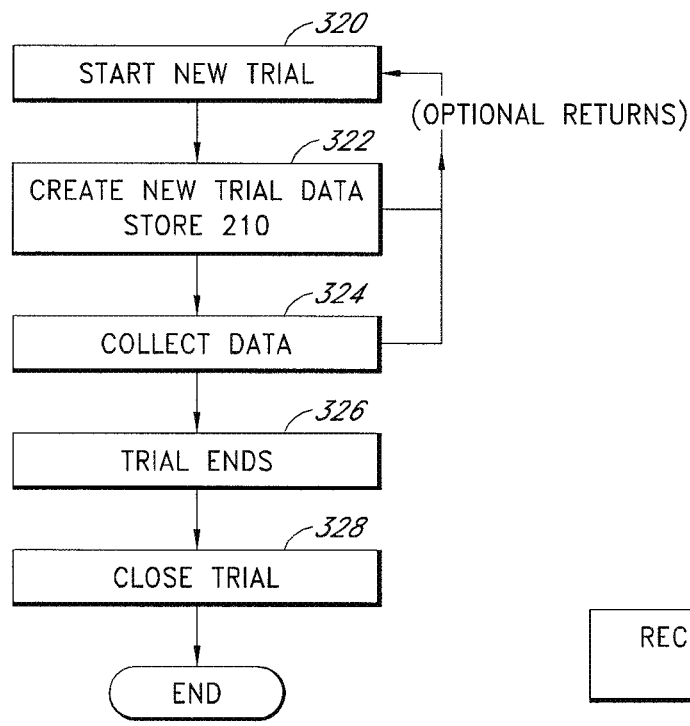
FIG. 3a illustrates a flow chart for managing clinical trial data according to an embodiment of the present disclosure.
Figure 3B:
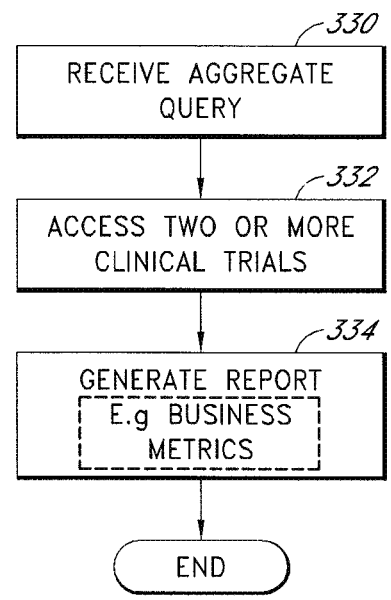
FIG. 3b illustrates a flow chart for aggregating clinical trial data according to an embodiment of the present disclosure.

FIGS. 3a and 3b, represent processes shown as flow diagrams. FIG. 3a illustrates the set-up and management of clinical trials utilizing an embodiment of the system disclosed herein. In Block 320, a new clinical trial is started. At this stage, a system administrator can access the system to set up management of a new clinical trial. For example, after a pharmaceutical company develops a new drug and gets it ready for testing, it may engage the services of a CRO, and testing parameters and study groups may be defined. A CRO system administrator can set up the clinical data store 102 to have a new trial data store 210 for the new trial (Block 322). This can be done by accessing server system 208 and having the processing module set up the new trial data store 210. The setup may include formatting a segment of an existing hard drive for the database, connecting to a new physical hard drive or server, or associating a previously created database with this one new trial. The system administrator can also set up logins and passwords on the system for doctors and hospitals to enter information about the new drug's testing. In an embodiment, the new trial data store 210 is populated with the latest code base 214 for interacting with the trial data store 210 or otherwise include a code base 214 associated therewith. At any point after a system administrator sets up a new clinical trial, he or she can return to the clinical data store 102 to set up additional trials which will be associated with different trial data stores 210.

Data collection for the clinical trials occurs in Block 324. The clinical data store 102 accepts data from remote data entry systems 106. In an embodiment, doctors, nurses, and technicians log onto the clinical data store 102 through the Internet in order to add new patients, update patient information, and/or convey observed, reported, or potential effects of the trial drug or treatment. In an embodiment, server system 208 of clinical data store 102 continuously monitors for doctors and trial participants to log into the system and update patient records. Any given trial will complete or otherwise be terminated (Block 326), and the system administrator may access server system 208 to close the trial (Block 328). In an embodiment, the server system no longer allows updates to the associated trial data store 210, Although the acceptance of additional data may be stopped, the trial data can remain in storage for a further duration, allowing data analysis and submission to the FDA. In an embodiment, the doctors, nurses, and/or technicians involved in gathering and reporting the data are allowed to review the trial data for a period of time after the clinical trial is completed.

FIG. 3b illustrates the segregation of various clinical trials, as discussed above, providing a more secure environment for managing clinical trials. The aggregation module 212 completes the system by allowing limited interactions between the clinical trials without harming the security of the individual trials. A CRO might wish to assess its efficiency and management of its clinical trials, perform other business metrics on the system, or assess potential treatment interactions thought to be occurring between two or more clinical trials. In Block 330, aggregation module 212 receives an Aggregate Query. Based on the type of information requested, the aggregation module 212 accesses at least two trial data stores 210 and preferably retrieves copies of the stored data (Block 332). In an embodiment, the aggregation module 212 only has read access to each trial data store 210 to reduce the possibility of data contamination. In an embodiment, aggregation module 212 does not have direct access to the trial data stores at all and instead works by making single or repeated queries to server system 208 to retrieve the necessary data. Once the aggregation module 212 has amassed the data, in Block 334, it can perform the data analysis for business metrics, drug interactions, and the like, and generate a report of the outcome.

Alternatives

Embodiments of the present disclosure will be known to those of skill in the art from the descriptions herein. For example, remote data entry system 106 can communicate with clinical data store 102 by means of a Universal Serial Bus (USB) or other direct connection. Communications network 104 includes networks, such as, for example, the Internet, a LAN, a WAN, a wireless network, a peer-to-peer network, or other suitable networks. Additionally, remote data entry systems 106 can work without a browser module. In an embodiment, remote data entry systems 106 run a stand-alone program capable of interacting with a network interface module or communications network 104 directly.

Additionally it the entire system and/or individual components can be validated by the FDA as mentioned more specifically in relation to the aggregation module 212.

Although the foregoing has been described in terms of certain preferred embodiments, other embodiments will be apparent to those of ordinary skill in the art from the disclosure herein. Moreover, the described embodiments have been presented by way of example only, and are not intended to limit the scope of the disclosure. Indeed, the novel methods and systems described herein may be embodied in a variety of other forms without departing from the spirit thereof. Accordingly, other combinations, omissions, substitutions and modifications will be apparent to the skilled artisan in view of the disclosure herein. Thus, the present disclosure is not limited by the preferred embodiments, but is defined by reference to the appended claims. The accompanying claims and their equivalents are intended to cover forms or modifications as would fall within the scope and spirit of the disclosure.

What is claimed is:

1. A system for a plurality of clinical trials, the system comprising:
    at least one computer readable medium encoded with:
        a plurality of clinical trial data stores, each of the plurality of clinical trial data stores associated with a clinical trial of the plurality of clinical trials;
        a first code base configured to, when executed on a server, capture first clinical trial data for a first clinical trial of the plurality of clinical trials;
        a second code base configured to, when executed on a server, capture second clinical trial data for a second clinical trial of the plurality of clinical trials, wherein the first and second code bases are executed without affecting each other; and
        an aggregation module configured to, when executed by a processor:
            read data from two or more clinical trial data stores of the plurality of clinical trial data stores;
            derive from the data information relating to at least one clinical trial associated with the plurality of clinical trial data stores; and
            output a report relating to improving clinical trial performance based on the derived information, wherein
            the processor constrains the execution of the aggregation module to components of the aggregation module such that the execution of the aggregation module does not affect data of the plurality of clinical trial data stores and the execution of the aggregation module does not affect either the execution of the first code base or the execution of the second code base.

2. The system of claim 1, wherein deriving from the data information relating to the at least one clinical trial associated with the plurality of clinical trial data stores comprises deriving information indicative of efficiencies in running trials.

3. The system of claim 1, wherein deriving from the data information relating to the at least one clinical trial associated with the plurality of clinical trial data stores comprises deriving business metrics indicative of efficiencies in running trials.

4. The system of claim 1, wherein deriving from the data information relating to the at least one clinical trial associated with the plurality of clinical trial data stores comprises deriving information related to trial interaction studies.

5. The system of claim 1, wherein deriving from the data information relating to the at least one clinical trial associated with the plurality of clinical trial data stores comprises deriving information related to monitoring clinical trials.

6. The system of claim 1, wherein deriving from the data information relating to the at least one clinical trial associated with the plurality of clinical trial data stores comprises deriving assessment of treatment interactions across clinical trials.

7. The system of claim 1, further comprising a plurality of discrete physical databases storing the plurality of clinical trial data stores.

8. The system of claim 7, wherein the aggregation module configured to, when executed by a processor, copy data from the discrete physical databases to a centralized location.

9. A system for a plurality of clinical trials at a plurality of disparate clinical trial locations, the system comprising:
    at least one non-transitory computer readable medium encoded with:
        a plurality of clinical trial data stores, each of the plurality of clinical trial data stores associated with a clinical trial location of the plurality of clinical trial locations;
        a plurality of code bases configured to, when executed on at least one processor, receive input comprising clinical trial data from a clinical trial location of the plurality of clinical trial locations and store it in a respective clinical trial data store of the plurality of clinical trial data stores, wherein the plurality of code bases are executed without affecting each other; and
        an aggregation module configured to, when executed by a processor:
            read data from two or more clinical trial data stores of the plurality of clinical trial data stores;
            derive from the data information relating to at least one clinical trial associated with the plurality of clinical trial data stores; and
            output a report relating to improving clinical trial performance based on the derived information, wherein
            the processor constrains the execution of the aggregation module to components of the aggregation module such that the execution of the aggregation module does not affect data of the plurality of clinical trial data stores.

10. The system of claim 9, wherein deriving from the data information relating to the at least one clinical trial associated with the plurality of clinical trial data stores comprises deriving information indicative of efficiencies in running trials.

11. The system of claim 9, wherein deriving from the data information relating to the at least one clinical trial associated with the plurality of clinical trial data stores comprises deriving business metrics.

12. The system of claim 9, wherein deriving from the data information relating to the at least one clinical trial associated with the plurality of clinical trial data stores comprises deriving business metrics indicative of efficiencies in running trials.

13. The system of claim 9, wherein deriving from the data information relating to the at least one clinical trial associated with the plurality of clinical trial data stores comprises assessing clinical trial interactions.

14. The system of claim 9, wherein deriving from the data information relating to the at least one clinical trial associated with the plurality of clinical trial data stores comprises deriving information related to trial interaction studies.

15. The system of claim 9, wherein deriving from the data information relating to the at least one clinical trial associated with the plurality of clinical trial data stores comprises deriving information related to improving efficiencies of clinical trials.

16. The system of claim 9, wherein deriving from the data information relating to the at least one clinical trial associated with the plurality of clinical trial data stores comprises deriving information related to monitoring clinical trials.

17. The system of claim 9, wherein deriving from the data information relating to the at least one clinical trial associated with the plurality of clinical trial data stores comprises deriving assessment of treatment interactions across clinical trials.

18. The system of claim 9, further comprising a plurality of discrete physical databases storing the plurality of clinical trial data stores.

19. A method of operating a computer system for a plurality of clinical trials at a plurality of disparate clinical trial locations, the method comprising:
- at each of the plurality of clinical trial locations, receiving input and storing, based on the input, clinical trial data in a respective clinical trial data store of a plurality of clinical trial data stores by executing a plurality of code bases, wherein the plurality of code bases are executed without
- affecting each other; and
- aggregating data from the plurality of clinical trial data stores, by:
  - reading data from two or more clinical trial data stores of the plurality of clinical trial data stores;
  - deriving from the data information relating to at least one clinical trial associated with the plurality of clinical trial data stores; and
  - outputting a report relating to improving clinical trial performance based on the derived information, wherein
  - the aggregating is constrained such that the aggregating does not affect clinical trial data of the plurality of clinical trial data stores, and
  - the aggregating is executed by a module configured for reading the data from the two or more clinical trial data stores via read only access.

20. The system of claim 19, wherein deriving from the data information relating to the at least one clinical trial associated with the plurality of clinical trial data stores comprises deriving information related to monitoring a clinical trial.

* * * * *